United States Patent [19]

Engel et al.

[11] Patent Number: 4,676,200
[45] Date of Patent: Jun. 30, 1987

[54] METHOD FOR USE DEPENDENT COMPLETE EVAPORATION OF LIQUID NITROGEN OXIDE

[75] Inventors: Richard Engel, Bornheim-Waldorf; Manfred Voll, Erlensee, both of Fed. Rep. of Germany

[73] Assignee: Degussa Aktiengesellschaft, Frankfurt am Main, Fed. Rep. of Germany

[21] Appl. No.: 772,486

[22] Filed: Sep. 4, 1985

[30] Foreign Application Priority Data

Sep. 11, 1984 [DE] Fed. Rep. of Germany ....... 3433301

[51] Int. Cl.⁴ .............................................. F22B 27/00
[52] U.S. Cl. ........................................ 122/39; 122/32
[58] Field of Search .................. 122/32, 39, 258, 4 R; 126/359; 202/236

[56] References Cited

U.S. PATENT DOCUMENTS

| | | | |
|---|---|---|---|
| 3,175,962 | 3/1965 | Holtslag | 122/39 X |
| 3,405,689 | 10/1968 | Petersen | 122/39 |
| 4,175,395 | 11/1979 | Prost et al. | 62/52 |
| 4,278,050 | 7/1981 | Kime | 122/39 |

Primary Examiner—Edward G. Favors
Attorney, Agent, or Firm—Beveridge, Degrandi & Weilacher

[57] ABSTRACT

A method for the consumption dependent complete vaporization of liquid nitrogen oxide is shown where the liquid nitrogen oxide under pressure is passed through a buffer tank and is charged into a falling film evaporator. The unevaporated residual amount of nitrogen oxide is then subjected to heat in an after evaporator in order to completely vaporize the nitrogen oxide. The combined streams are then led out of the falling film evaporator and after evaporator through at least one safety trap to the ultimate take-off points. This results in the charge of the liquid material to the falling film evaporator being controlled through the pressure in the conduit system between the falling film evaporator and the points of utilization and permits a constant, previously determined pressure to be maintained in the system independently of the amount of material withdrawn.

6 Claims, 1 Drawing Figure

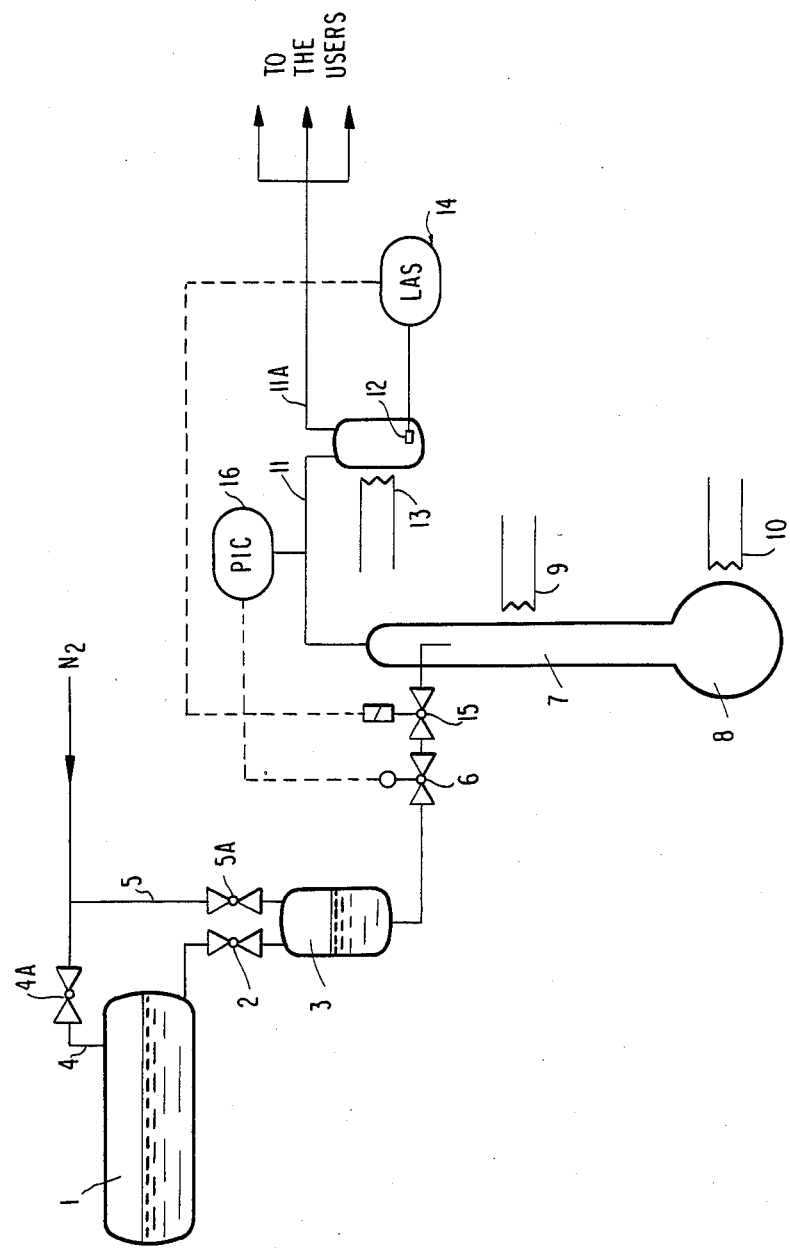

METHOD FOR USE DEPENDENT COMPLETE EVAPORATION OF LIQUID NITROGEN OXIDE

The present invention relates to a method for the consumption dependent complete vaporization of liquid nitrogen oxide consisting predominantly of $N_2O_4$ for the furnishing of this gas for chemical reactions, such as for example, an oxidation of the surface areas of carbon black.

For the large scale commercial production of conversions and treatments with gaseous oxides of nitrogen $N_2O_4$ particularly $NO_2$, it is necessary to provide a larger stream of material of these reactants and to maintain this quantity over a longer period of time. While the withdrawal of a smaller quantity streams of nitrogen oxides out of the gaseous space of conventional transport or storage containers that are filled with liquid nitrogen oxide may be accomplished without encountering difficulties, when it is desired to provide larger streams of such material the vaporization that takes place at normal ambient temperatures is not sufficient and therefore, the vaporization process must be speeded up by heating the source of supply. In view of the intrusiveness and toxicity of this material, the need for warming of a large volume of the liquid creates a safety hazard.

Over and above that, a cooling off of the liquid takes place during the vaporization resulting in a lowering of the vapor pressure and a further reduction in the pressure of the vaporized nitrogen oxides, the greater the removal of quantities of material is. As a result of the changing form, there must therefore be a measuring and control of the flowing gas quantities to one or more points of application or use which must be continuously corrected. Because of the pressure and temperature dependent dissociation of the gaseous dinitrogen tetraoxide this is hardly possible at all without costly computer regulated controls.

Moreover, a stored large volume of the liquid nitrogen oxide when subjected to heat responds only with a certain delay so that with the changing amounts of withdrawal, a constant vaporization temperature and therefore a constant vapor pressure is not achievable without delays.

Furthermore, the heating of a large amount of liquid nitrogen oxides creates a danger in that through delays in boiling, liquid reagents in the vapor conduit lines and therefore also at the take-off points for utilization will blast through causing problems. In view of the reactivity of nitrogen oxides this could lead to uncontrollable reactions.

As a result thereof, there has been prior to this invention an urgent need to provide a method for an essentially delay free, use dependent complete vaporization of liquid nitrogen oxides predominantly consisting of $N_2O_4$ so that the above mentioned difficulties are avoided.

This object is achieved in accordance with the present invention by means of a method comprising providing liquid nitrogen oxide in a storage facility and conducting the liquid nitrogen oxide through a buffer tank and thereafter introducing the liquid nitrogen oxide into a falling film evaporator. After passage through the falling zone of the evaporator any unevaporated remaining residual amounts of nitrogen oxide are conveyed to an after evaporator which is connected to the outlet pipe at the bottom end of the falling film evaporator and said residual amounts are there evaporated. The combined vapor streams from the falling film evaporator and the after evaporator are then conveyed to the take-off points at which the gaseous nitrogen oxide product is removed by means of at least one heated safety trap equipped with a liquid detector means. In this manner, the liquid feed rate to the falling film evaporator is controlled through the pressure in the thoroughly heated production system between the falling film evaporator and the take-off points at which the gaseous nitrogen oxide product is removed. As a result thereof, a constant predetermined pressure can be maintained in the system at the take-off point independent of the amount of material that is removed at the point of removal.

The method of the present invention is further illustrated in this following embodiment which provides for supplying nitrogen oxide in a large number of installations for the oxidative after treatment of carbon blacks with nitrogen oxide-containing gases, and in combination with the drawing which shows in schematic representation a flow diagram of a method for carrying out the present invention.

In accordance with the accompanying drawing, there is provided a storage tank (1) for holding and containing a large quantity of liquid nitrogen oxide and which is provided with a conduit leading to a closure device or valve (2) which in turn is connected to a buffer tank (3). The holding tank and the buffer tank may be of conventional design. In the embodiment shown in the drawing, it is possible to impose a pressure on the storage tank (1) and the buffer tank (3) by means of the conduit line (4) and (5) which are connected to a source of nitrogen or another inert gas, there being another control valve (4A) in conduit line (4). Line (5) is also provided with control valve (5A). The source of pressure for the storage tank (1) and the buffer tank (3) is provided in order to overcome the counter pressure in the vaporization equipment which is connected thereto further downstream. The free space above the liquid nitrogen oxide in vessels 1 and 3 is filled with inert gas. This gas exerts a pressure on the liquid nitrogen oxide and forces the liquid nitrogen oxide into the apparatus of the system with a super atmospheric pressure of about 2.5 bar. The pressure in the tanks 1 and 3 can range from 0.5 to 4 bar, preferably 1.5 to 3 bar and most preferably about 2.5 bar. The pressure within the system downstream therefrom is lower than the pressure in vessels 1 and 3. From the buffer tank (3), the liquid nitrogen oxide is conveyed through the control valve (6) to a distributing head of any suitable form (not shown) at the top of the vaporization device. The latter comprises a falling film evaporator section (7) which has connected at its outflow pipe at the lower end thereof an after evaporator (8) which is provided for vaporizing any unevaporated remaining residual amounts of nitrogen oxide which flow down from the falling film evaporator. Falling film evaporator and the after evaporator are provided with heating elements 9 and 10, respectively, and are heated to temperature above that boiling point which is determined by the given gas pressure of the nitrogen oxide. The conditions for temperature and pressure in the evaporator (7) are, for example, 1.8 bar pressure and 80°–90° C. The evaporator is heated from the outside with steam of approximately 0.4 bar super atmospheric pressure. The equipment and the conditions under which such equipment functions are known in the art and can be varied as will be apparent to those skilled in the art.

The vaporized nitrogen oxide which is obtained in the falling film evaporator and the after evaporator is then conveyed through the heated conduit line (11) at the head of the falling film evaporator section (7) through a safety trap (12) which is heated by heating means (13) and through line (11A), which optionally may be heated, to the individual users of the nitrogen oxide which may be at various points and locations. The safety trap is provided in its bottom portion with a liquid detector or sensor (14) designated as "LAS" denoting thereby level alarm switch (for example one of the various known devices which measure the refractive index of liquids or vapor determining optical apparatus) which in the event of a disturbance or problem caused in the safety trap by a blast of the liquid nitrogen oxide operates an alarm and/or quickly cuts off the liquid feed to the falling film evaporator through the rapidly closing valve (15).

A constant predetermined pressure in the system before the points at which the users take off the nitrogen oxide is thereby obtainable through a pressure measurement and control instrument (PIC—pressure indication and control) 16 which regulates the control valve (6).

Through the utilization of the control valve (6), the pressure controlled nitrogen oxide which is charged to the falling film evaporator (7) and the after evaporator (8) is completely vaporized and as a result thereof there exists in the conduit lines (11) and (11A) which convey the gaseous nitrogen oxide to the points of distribution, a predetermined pressure which is essentially without delay independent of the amounts of material withdrawn and is constantly maintained.

Described in further detail, valve (6) is controlled by means of the PIC using the gas pressure in line (11) as the signal. The nominal valve set on PIC is preliminarily adjusted by the operator. Thereafter, the PIC operates automatically. The gas pressure in line (11) is generated by the liquid nitrogen oxide vaporizing in evaporator (7). To maintain the desired pressure in line (11), the influx of liquid nitrogen oxide is regulated by PIC which regulates valve (6). The preselected gas pressure in the system is established and maintained by charging evaporator (7) with liquid nitrogen oxide. This charging is regulated through the PIC controlled valve (6).

As an alternative, there can be utilized instead of the control valve 6, a pressure dependent controlled measuring pump. Thereby, it is possible under selected conditions to avoid the possibility of the evaporation of the nitrogen oxide on the suction side of the pump wherein there is a pressure applied of nitrogen oxide in the conduit lines (4) and (5).

Buffer tank (3) is an intermediate vessel which can have the following functions: (a) during the operation of the process, the level of the liquid nitrogen oxide in tank (1) is in general, subject to a certain amount of movement and therefore, the buffer tank takes over the function of maintaining a constant nitrogen oxide supply to the apparatus; (b) it may contain a filling level alarm system whereby an emptying of vessel (1) would result in a short fall of liquid nitrogen oxide below a preselected filling level in vessel (3) causing an alarm to indicate a low level.

The falling film evaporator and the after evaporator used in accordance with the present invention are of conventional design and any such suitable apparatus may be used for the purposes described herein.

Further variations and modifications of the foregoing invention will become apparent to those skilled in the art from a reading of the foregoing.

The entire disclosure of the German patent application No. P 34 33 301.0 filed Sept. 11, 1984 is relied and incorporated herein by reference.

We claim:

1. A method for the control of the vaporization of liquid nitrogen oxide depending upon the amount of gaseous nitrogen oxide withdrawn at a distribution point comprising providing liquid nitrogen oxide in a storage vessel, conveying said nitrogen oxide to a buffer tank and then via a control valve into a falling film evaporator wherein said liquid nitrogen is vaporized, any unevaporated residual amount of nitrogen oxide proceeding directly from the falling film evaporator to an after evaporator which vaporizes this residual amount of liquid nitrogen oxide, combining the vapor streams from the falling film evaporator and the after evaporator and conveying said combined vapor streams through at least one heated safety trap fitted with a liquid detecting means to the point of distribution, the flow rate of liquid nitrogen oxide to the falling film evaporator being controlled by the pressure between the falling film evaporator and the point distribution of the food rate of liquid nitrogen oxide to the evaporator is adjusted to be equal to the consumption of gaseous nitrogen oxide at the distribution points, thus maintaining a constant predetermined pressure at said distributor point.

2. The method of claim 1 further comprising heating the vaporized nitrogen oxide between the evaporator and the point of distribution.

3. The method of claim 1 further comprising controlling the pressure through automatic valve means.

4. The method of claim 1 wherein said liquid detecting means in said safety trap is enabled to quickly cut off the feed of liquid nitrogen oxide to the evaporator.

5. An apparatus for the complete vaporization of nitrogen oxides comprising a vessel for retaining liquid nitrogen oxide connected to a buffer tank, said vessel and tank both being connected to a source of inert gas, said buffer tank being connected through valve means to evaporation means being a falling film evaporator connected at its lower end to an after evaporation, said evaporation means having inlet means for the liquid and outlet means for the gas and being connected through conduit means to a safety trap with means for detecting unvolatilized liquid, and said safety trap being connected to at least one conduit for take-off of the gaseous product, controlling means being directly connected to said valve means and provided at the outlet of said evaporating means to measure pressure in said conduit means, compare the measured pressure to a predetermined value and control the amount of liquid feed to the evaporator means.

6. The apparatus of claim 5 wherein said means for detecting unvolatilized liquid in the safety trap means is connected with means to a rapidly closing valve for cutting off the flow of liquid to inlet means on said evaporator in the event of distribution.

* * * * *